United States Patent
Sun et al.

(10) Patent No.: US 9,187,386 B2
(45) Date of Patent: Nov. 17, 2015

(54) CATALYTIC PROCESS OF MAKING 1,3,3,3-TETRAFLUOROPROPENE

(71) Applicant: E I DU PONT DE NEMOURS AND COMPANY, Wilmington, DE (US)

(72) Inventors: Xuehui Sun, Kennett Square, PA (US); Mario Joseph Nappa, Newark, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 0 days.

(21) Appl. No.: 14/275,934

(22) Filed: May 13, 2014

(65) Prior Publication Data

US 2014/0350310 A1 Nov. 27, 2014

Related U.S. Application Data

(60) Provisional application No. 61/826,611, filed on May 23, 2013.

(51) Int. Cl.
C07C 17/23 (2006.01)
C07C 17/25 (2006.01)

(52) U.S. Cl.
CPC .............. *C07C 17/23* (2013.01); *C07C 17/25* (2013.01)

(58) Field of Classification Search
CPC .............................. C07C 17/23; C07C 17/25
USPC .................. 570/155, 156, 157, 158
See application file for complete search history.

(56) References Cited

U.S. PATENT DOCUMENTS

| 7,803,973 B2 | 9/2010 | Merkel et al. |
| 7,829,748 B1 | 11/2010 | Tung et al. |
| 7,880,040 B2 | 2/2011 | Mukhopadhyay et al. |
| 7,985,884 B2 * | 7/2011 | Nappa et al. ............ 570/157 |
| 8,115,037 B2 | 2/2012 | Sakyu et al. |
| 8,513,474 B2 * | 8/2013 | Wang et al. ............ 570/156 |
| 2007/0129579 A1 | 6/2007 | Wang et al. |
| 2007/0129580 A1 | 6/2007 | Mukhopadhyay et al. |
| 2008/0051611 A1 | 2/2008 | Wang et al. |

FOREIGN PATENT DOCUMENTS

| EP | 2327680 | 6/2011 |
| WO | 2009048048 A1 | 4/2009 |

OTHER PUBLICATIONS

International Search Report, PCT/US2014/039093, Mailed on Nov. 14, 2014.

* cited by examiner

*Primary Examiner* — Shailendra Kumar

(57) ABSTRACT

This disclosure relates to processes of making 1,3,3,3-tetrafluoropropene. The processes involve dehydrofluorinating 1,1,1,3,3-pentafluoropropane in vapor phase in the presence of a catalyst comprising a metal compound supported on alumina to produce a product mixture comprising 1,3,3,3-tetrafluoropropene, wherein said metal compound is selected from the group consisting of salts of sodium, potassium, zinc, magnesium, calcium, cobalt, copper, and chromium, and mixtures thereof.

14 Claims, No Drawings

CATALYTIC PROCESS OF MAKING 1,3,3,3-TETRAFLUOROPROPENE

This application claims benefit of 61/826,611, filed on May 23, 2013.

BACKGROUND

1. Field of the Disclosure

The present disclosure relates to a catalytic process of making 1,3,3,3-tetrafluoropropene ($CF_3CH=CHF$, HFO-1234ze) by using a metal compound supported on alumina.

2. Description of Related Art

Many industries have been working for the past few decades to find replacements for the ozone depleting chlorofluorocarbons (CFCs) and hydrochlorofluorocarbons (HCFCs). The CFCs and HCFCs have been employed in a wide range of applications, including their use as aerosol propellants, refrigerants, cleaning agents, expansion agents for thermoplastic and thermoset foams, heat transfer media, gaseous dielectrics, fire extinguishing and suppression agents, power cycle working fluids, polymerization media, particulate removal fluids, carrier fluids, buffing abrasive agents, and displacement drying agents. In the search for replacements for these versatile compounds, many industries have turned to the use of hydrofluorocarbons (HFCs).

The HFCs do not contribute to the destruction of stratospheric ozone, but are of concern due to their contribution to the "greenhouse effect", i.e., they contribute to global warming. As a result of their contribution to global warming, the HFCs have come under scrutiny, and their widespread use may also be limited in the future. Thus, there is a need for chemical compounds that do not contribute to the destruction of stratospheric ozone and also have low global warming potentials (GWPs).

BRIEF SUMMARY OF THE DISCLOSURE

The present disclosure provides a process for making 1,3,3,3-tetrafluoropropene. The process comprises dehydrofluorinating 1,1,1,3,3-pentafluoropropane in vapor phase in the presence of a catalyst comprising a metal compound supported on alumina to produce a product mixture comprising 1,3,3,3-tetrafluoropropene, wherein said metal compound is selected from the group consisting of salts of sodium, potassium, zinc, magnesium, calcium, cobalt, copper, and chromium, and mixtures thereof.

DETAILED DESCRIPTION

Hydrofluoroolefins (HFOs) have been found to have low ODPs and low GWPs and have been regarded as potential replacements for HFCs in many applications. For example, $CF_3CH=CHF$ (1,3,3,3-tetrafluoropropene, HFO-1234ze), having zero ODPs and low GWPs, has been identified as potential refrigerants and foam expansion agents.

The foregoing general description and the following detailed description are exemplary and explanatory only and are not restrictive of the invention, as defined in the appended claims. Other features and benefits of any one or more of the embodiments will be apparent from the following detailed description, and from the claims.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. In case of conflict, the present specification, including definitions, will control. Although methods and materials similar or equivalent to those described herein can be used in the practice or testing of embodiments of the present invention, suitable methods and materials are described below. In addition, the materials, methods, and examples are illustrative only and not intended to be limiting.

When an amount, concentration, or other value or parameter is given as either a range, preferred range or a list of upper preferable values and/or lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range.

Before addressing details of embodiments described below, some terms are defined or clarified.

HFO-1234ze may exist as one of two configurational isomers, E or Z. HFO-1234ze as used herein refers to the isomers, E-HFO-1234ze or Z-HFO-1234ze, as well as any combinations or mixtures of such isomers.

The term "an elevated temperature", as used herein, means a temperature higher than the room temperature.

The term "dehydrofluorination", "dehydrofluorinating" or "dehydrofluorinated", as used herein, means a process during which hydrogen and fluorine on adjacent carbons in a molecule are removed.

The term "selectivity to 1,3,3,3-tetrafluoropropene", as used herein, means the molar percentage of HFO-1234ze obtained in the dehydrofluorination reaction of 1,1,1,3,3-pentafluoropropane ($CF_3CH_2CHF_2$, HFC-245fa) compared to the total molar amount of all products obtained.

The present disclosure provides a process for making HFO-1234ze. The process comprises dehydrofluorinating HFC-245fa in vapor phase in the presence of a catalyst comprising a metal compound supported on alumina to produce a product mixture comprising HFO-1234ze, wherein said metal compound is selected from the group consisting of salts of sodium, potassium, zinc, magnesium, calcium, cobalt, copper, and chromium, and mixtures thereof.

The catalytic dehydrofluorination of HFC-245fa may possibly generate byproducts, such as HFC-143 ($C_2H_3F_3$), trifluoropropyne ($CF_3C\equiv CH$), HFC-245cb ($CF_3CF_2CH_3$), HFO-1234yf ($CF_3CF=CH_2$), and HFC-152a($CH_3CHF_2$), along with the desired product HFO-1234ze. It was surprisingly found through experiments that the catalyst comprising metal compound supported on alumina can produce HFO-1234ze with higher selectivity than other metal catalysts. In some embodiments of this invention, the catalyst consists essentially of metal compound supported on alumina.

In some embodiments of this invention, the selectivity to HFO-1234ze is at least about 99.0 mole %. In some embodiments of this invention, the selectivity to HFO-1234ze is at least about 99.5 mole %. In some embodiments of this invention, the selectivity to HFO-1234ze is at least about 99.8 mole %.

Alumina ($Al_2O_3$) exists in several different phases, e.g., α-, γ-, δ-, η-, θ-, and χ-aluminas. In α-$Al_2O_3$ (corundum), the oxide ions form a hexagonal close-packed structure and the aluminum ions are distributed symmetrically among the octahedral interstices (see F. A. Cotton and G. Wilkinson, *Advanced Inorganic Chemistry, Fifth Edition*, John Wiley & Sons, 1988, page 211). γ-$Al_2O_3$ has a "defect" spinel structure (the structure of spinel with a deficit of cations). Id. In some embodiments of this invention, at least 95% of the alumina carrier in the catalyst is γ-$Al_2O_3$. In some embodiments of this invention, at least 98% of the alumina carrier in the catalyst is γ-$Al_2O_3$. In some embodiments of this invention, the alumina carrier in the catalyst consists essentially of γ-$Al_2O_3$.

Alumina may be prepared by methods known in the art. For example, the Bayer process is widely used in the industry to produce alumina from bauxite. α-$Al_2O_3$ can be prepared by heating γ-$Al_2O_3$ or any hydrous oxide above 1000° C. Id. γ-$Al_2O_3$ can be prepared by dehydration of hydrous oxides at about 450° C. Id.

The alumina used in this disclosure can be of any suitable shape and dimensions. For example, alumina can be in the form of powder, granules, spheres, or tablets, et al. Typically, alumina used in this disclosure has surface area of from about 75 $m^2/g$ to about 300 $m^2/g$. In some embodiments of this invention, the alumina has surface area of from about 90 $m^2/g$ to about 250 $m^2/g$. In some embodiments of this invention, the alumina has surface area of from about 160 $m^2/g$ to about 240 $m^2/g$.

The metal compound in this disclosure is selected from the group consisting of salts of sodium, potassium, zinc, magnesium, calcium, cobalt, copper, and chromium, and mixtures thereof. In some embodiments of this invention, the salts are inorganic salts such as halides, bicarbonates, carbonates, nitrates, oxides, and oxyfluorides. In some embodiments of this invention, the salts are organic salts such as acetates, and oxalates. In some embodiments of this invention, the metal compound is selected from the group consisting of halides, bicarbonates, carbonates, nitrates, oxides, and oxyfluorides of sodium, potassium, zinc, magnesium, calcium, cobalt, copper, and chromium, and mixtures thereof. In some embodiments of this invention, the metal compound is selected from the group consisting of inorganic salts of potassium, zinc, and magnesium, and mixtures thereof. In some embodiments of this invention, the metal compound is selected from the group consisting of $ZnCl_2$, $KHCO_3$, $MgCl_2$, and mixtures thereof.

In some embodiments of this invention, the concentration of the metal compound is from about 0.1 wt % to about 5 wt % based on the total weight of the metal compound and the alumina carrier. In some embodiments of this invention, the concentration of the metal compound is from about 0.2 wt % to about 3 wt %.

These metal doped catalysts can be made using techniques known in the art. In some embodiments of this invention, the catalysts may be prepared by slurring dried alumina with an aqueous solution of a metal salt, such as magnesium chloride, zinc chloride or potassium bicarbonate. An agitator is typically used to help the uniform adsorption of the metal salt onto alumina. The slurry is then allowed to dry, typically at an elevated temperature under nitrogen.

Optionally, the catalyst is pre-treated with a fluorinating agent prior to use as the dehydrofluorination catalyst. Typically this fluorinating agent is HF though other materials may be used such as sulfur tetrafluoride, carbonyl fluoride, and fluorinated hydrocarbon compounds such as trichlorofluoromethane, dichlorodifluoromethane, chlorodifluoromethane, trifluoromethane, or 1,1,2-trichlorotrifluoroethane. This pretreatment can be accomplished, for example, by placing the dried catalyst in a suitable container which can be the reactor to be used to perform the dehydrofluorination process in the instant invention, and thereafter, passing HF over the dried catalyst so as to partially saturate the catalyst with HF. This is conveniently carried out by passing HF over the catalyst for a period of time, for example, about 0.1 to about 16 hours at a temperature of, for example, about 200° C. to about 450° C.

The vapor phase dehydrofluorination process in this disclosure can be carried out using well-known chemical engineering practice, which includes continuous, semi-continuous or batch operations. In some embodiments of this invention, HFC-245fa, optionally with a diluent, is passed through the catalyst bed in a reactor.

In some embodiments of this invention, the vapor phase dehydrofluorination process is conducted without a diluent.

In some embodiments of this invention, the vapor phase dehydrofluorination process is conducted in the presence of a diluent. In some embodiments of this invention, the diluent is co-fed to the reactor with the HFC-245fa starting material. In some embodiments of this invention, the molar ratio of the diluent to the HFC-245fa starting material co-fed to the reactor is from about 5:1 to about 0.5:1. The diluent can be an inert gas which does not react under the dehydrofluorination conditions of this disclosure. In some embodiments of this invention, the diluent is He, Ar, or $N_2$. In some embodiments of this invention, the diluent is $N_2$.

In some embodiments of this invention, the dehydrofluorination process is conducted in the presence of oxygen. In some embodiments of this invention, the dehydrofluorination process is conducted in the presence of air. In some embodiments of this invention, air is co-fed with HFC-245fa into the reactor. It was found that the presence of oxygen or air during the process can extend the life of the catalyst.

The vapor phase dehydrofluorination process in this disclosure is typically conducted at a temperature of from about 200° C. to about 350° C. In some embodiments of this invention, the dehydrofluorination process is conducted at a temperature of from about 250° C. to about 325° C. In some embodiments of this invention, the dehydrofluorination process is conducted at a temperature of from about 250° C. to about 300° C. The contact time of the HFC-245fa with the catalyst during the dehydrofluorination process in this disclosure is typically from about 1 to about 450 seconds. In some embodiments of this invention, the contact time is from about 10 to about 120 seconds.

In some embodiments of this invention, the catalyst comprises an inorganic salt of zinc supported on alumina, the dehydrofluorination process is conducted at a temperature of from about 250° C. to about 350° C., and the selectivity to 1234ze is at least about 99.0 mole %. In some embodiments of this invention, such dehydrofluorination process is conducted at a temperature of from about 275° C. to about 325° C., and the selectivity to 1234ze is at least about 99.0 mole %. In some embodiments of this invention, such dehydrofluorination process is conducted at a temperature of from about 300° C. to about 325° C., and the selectivity to 1234ze is at least about 99.8 mole %. Optionally, these processes can be conducted in the presence of oxygen or air. The representative zinc salt in above processes is $ZnCl_2$.

In some embodiments of this invention, the catalyst comprises an inorganic salt of potassium supported on alumina, the dehydrofluorination process is conducted at a temperature of from about 250° C. to about 350° C., and the selectivity to 1234ze is at least about 99.5 mole %. In some embodiments of this invention, such dehydrofluorination process is conducted at a temperature of from about 275° C. to about 325° C., and the selectivity to 1234ze is at least about 99.7 mole %. In some embodiments of this invention, such dehydrofluorination process is conducted at a temperature of from about 300° C. to about 325° C., and the selectivity to 1234ze is at least about 99.7 mole %. Optionally, these processes can be conducted in the presence of oxygen or air. In some embodiments of this invention, such dehydrofluorination process is conducted at a temperature of from about 250° C. to about 325° C. in the presence of oxygen or air, and the selectivity to 1234ze is at least about 99.8 mole %. In some embodiments of this invention, such dehydrofluorination process is conducted at a temperature of from about 275° C. to about 325° C. in the presence of oxygen or air, and the selectivity to 1234ze is at least about 99.8 mole %. In some embodiments of this invention, such dehydrofluorination process is conducted at a temperature of from about 300° C. to about 325° C. in the presence of oxygen or air, and the selectivity to 1234ze is at least about 99.8 mole %. The representative potassium salt in above processes is $KHCO_3$.

In some embodiments of this invention, the catalyst comprises an inorganic salt of magnesium supported on alumina, the dehydrofluorination process is conducted at a temperature of from about 250° C. to about 350° C., and the selectivity to 1234ze is at least about 99.8 mole %. In some embodiments of this invention, such dehydrofluorination process is conducted at a temperature of from about 300° C. to about 325° C., and the selectivity to 1234ze is at least about 99.8 mole %.

The reaction pressure can be subatmospheric, atmospheric or superatmostpheric. Generally, near atmospheric pressures are preferred. However, the dehydrofluorination can be beneficially run under reduced pressure (i.e., pressures less than one atmosphere).

The effluent from the vapor phase dehydrofluorination reactor is typically a product mixture comprising unreacted HFC-245fa, diluent (if used in the process), HFO-1234ze and some byproducts. HFO-1234ze may be recovered from the product mixture by conventional methods. In some embodiments of this invention, HFO-1234ze may be purified or recovered by distillation. In some embodiments of this invention, the unreacted HFC-245fa, and optionally diluent (if used in the process), are recovered and recycled back to the reactor.

The reactors, distillation columns, and their associated feed lines, effluent lines, and associated units used in applying the processes of embodiments of this invention may be constructed of materials resistant to corrosion. Typical materials of construction include Teflon™ and glass. Typical materials of construction also include stainless steels, in particular of the austenitic type, the well-known high nickel alloys, such as Monel™ nickel-copper alloys, Hastelloy™ nickel-based alloys, and Inconel™ nickel-chromium alloys, and copper-clad steel.

Many aspects and embodiments have been described above and are merely exemplary and not limiting. After reading this specification, skilled artisans appreciate that other aspects and embodiments are possible without departing from the scope of the invention.

EXAMPLES

The concepts described herein will be further described in the following examples, which do not limit the scope of the invention described in the claims.

$Al_2O_3$ used in the examples below was purchased from BASF with surface area of about 230 $m^2/g$.

In the examples the follow abbreviations or codes may be used:
sec=second
sccm=Standard Cubic Centimeters per Minute
245fa=$CF_3CH_2CHF_2$
1234ze=$CF_3CH=CHF$
Catalyst Preparation Preparation Example 1

Preparation of 2% Zn Supported on Alumina $Al_2O_3$ was crushed and sieved to 12-20 mesh and dried at 125° C. for 4 hours then 250° C. for 4 hours under nitrogen. 0.833 grams of $ZnCl_2$ were dissolved in 24.2 grams of water, and the solution was poured into a beaker containing 20 grams of dried $Al_2O_3$. The mixture was agitated until all of the $ZnCl_2$ solution was absorbed by the $Al_2O_3$. The resulting catalyst was air dried then dried at 125° C. for 4 hours then 250° C. for 4 hours under nitrogen.

Preparation Example 2

Preparation of 0.2% K Supported on Alumina $Al_2O_3$ was crushed and sieved to 12-20 mesh and dried at 250° C. for 4 hours under nitrogen. 0.1024 grams of $KHCO_3$ were dissolved in 16.2 grams of water, and the solution was poured into a beaker containing 20 grams of dried $Al_2O_3$. The mixture was agitated until all of the $KHCO_3$ solution was absorbed by the $Al_2O_3$. The resulting catalyst was air dried then dried at 125° C. for 4 hours then 250° C. for 4 hours under nitrogen.

Preparation Example 3

Preparation of 0.2% Mg Supported on Alumina $Al_2O_3$ was crushed and sieved to 12-20 mesh and dried at 250° C. for 4 hours under nitrogen. 0.0783 grams of $MgCl_2$ were dissolved in 13.0 grams of water, and the solution was poured into a beaker containing 10 grams of dried $Al_2O_3$. The mixture was agitated until all of the $ZnCl_2$ solution was absorbed by the $Al_2O_3$. The resulting catalyst was air dried then dried at 125° C. for 4 hours then 250° C. for 4 hours under nitrogen.
Catalytic Dehydrofluorination Reaction Example 4

Example 4 demonstrates the catalytic dehydrofluorination of HFC-245fa over the zinc doped $Al_2O_3$ catalyst.

5 cc Zinc doped $Al_2O_3$ catalyst, prepared as described in Preparation Example 1, was loaded into a ½ inch Hastelloy C 227 reactor tube. The catalyst was first treated with HF at 325° C. for about 13 hours. Then HFC-245fa was fed into the reactor tube at the rate of 2.5 ml/hr at the 35 psig back pressure. The temperature of the reactor tube was maintained at 250° C., 275° C., 300° C. and 325° C. respectively for a series of test runs and the effluent from the reactor tube was analyzed by GC and GC-MS. The results of the reaction at various temperatures are shown in Table 1.

TABLE 1

| Run | Temp. (° C.) | 245fa Conversion (%) | Selectivity to 1234ze (mole %) |
|---|---|---|---|
| 1 | 250 | 22.6 | 99.5 |
| 2 | 275 | 36.5 | 99.7 |
| 3 | 300 | 52.3 | 99.8 |
| 4 | 325 | 67.1 | 99.9 |

Example 5 (Comparative)

Example 5 demonstrates the catalytic dehydrofluorination of HFC-245fa over the non-doped $Al_2O_3$ catalyst.

5 cc $Al_2O_3$, after crushed and sieved to 12-20 mesh, was loaded into a ½ inch Hastelloy C 227 reactor tube and dried at 325° C. for 2 hours under nitrogen. The catalyst was first treated with HF at 325° C. for about 13 hours. Then HFC-245fa was fed into the reactor tube at the rate of 2.5 ml/hr at the 35 psig back pressure. The temperature of the reactor tube was maintained at 250° C., 275° C., 300° C. and 325° C. respectively for a series of test runs and the effluent from the reactor tube was analyzed by GC and GC-MS. The results of the reaction at various temperatures are shown in Table 2.

TABLE 2

| Run | Temp. (° C.) | 245fa Conversion (%) | Selectivity to 1234ze (mole %) |
|---|---|---|---|
| 1 | 250 | 25.7 | 99.4 |
| 2 | 275 | 37.9 | 99.6 |
| 3 | 300 | 52.4 | 99.6 |
| 4 | 325 | 66.9 | 99.6 |

Example 6

Example 6 demonstrates the catalytic dehydrofluorination of HFC-245fa over the zinc doped $Al_2O_3$ catalyst in the presence of air.

5 cc Zinc doped $Al_2O_3$ catalyst, prepared as described in Preparation Example 1, was loaded into a ½ inch Hastelloy C 227 reactor tube. The catalyst was first treated with HF at 325° C. for about 13 hours. Then HFC-245fa was co-fed into the reactor tube with air at the 35 psig back pressure. HFC-245fa was fed at the rate of 4 ml/hr, and air was fed at the rate of 3 sccm. The temperature of the reactor tube was maintained at 275° C., 300° C. and 325° C. respectively for a series of test runs and the effluent from the reactor tube was analyzed by GC and GC-MS. The results of the reaction at various temperatures are shown in Table 3.

TABLE 3

| Run | Temp. (° C.) | 245fa Conversion (%) | Selectivity to 1234ze (mole %) |
|---|---|---|---|
| 1 | 275 | 31.7 | 99.2 |
| 2 | 300 | 49.3 | 99.8 |
| 3 | 325 | 66.7 | 99.9 |

Example 7 (Comparative)

Example 7 demonstrates the catalytic dehydrofluorination of HFC-245fa over the non-doped $Al_2O_3$ catalyst in the presence of air.

5 cc $Al_2O_3$, after crushed and sieved to 12-20 mesh, was loaded into a ½ inch Hastelloy C 227 reactor tube and dried at 325° C. for 2 hours under nitrogen. The catalyst was first treated with HF at 325° C. for about 13 hours. Then HFC-245fa was co-fed into the reactor tube with air at the 35 psig back pressure. HFC-245fa was fed at the rate of 4 ml/hr, and air was fed at the rate of 3 sccm. The temperature of the reactor tube was maintained at 250° C., 275° C., 300° C. and 325° C. respectively for a series of test runs and the effluent from the reactor tube was analyzed by GC and GC-MS. The results of the reaction at various temperatures are shown in Table 4.

TABLE 4

| Run | Temp. (° C.) | 245fa Conversion (%) | Selectivity to 1234ze (mole %) |
|---|---|---|---|
| 1 | 250 | 26.6 | 99.6 |
| 2 | 275 | 40.6 | 99.7 |
| 3 | 300 | 55.7 | 99.7 |
| 4 | 325 | 70.0 | 99.1 |

Example 8

Example 8 demonstrates the catalytic dehydrofluorination of HFC-245fa over the potassium doped $Al_2O_3$ catalyst.

5 cc Potassium doped $Al_2O_3$ catalyst, prepared as described in Preparation Example 2, was loaded into a ½ inch Hastelloy C 227 reactor tube. The catalyst was first treated with HF at 325° C. for about 13 hours. Then HFC-245fa was fed into the reactor tube at the rate of 2.5 ml/hr at the 35 psig back pressure. The temperature of the reactor tube was maintained at 250° C., 275° C., 300° C. and 325° C. respectively for a series of test runs and the effluent from the reactor tube was analyzed by GC and GC-MS. The results of the reaction at various temperatures are shown in Table 5.

TABLE 5

| Run | Temp. (° C.) | 245fa Conversion (%) | Selectivity to 1234ze (mole %) |
|---|---|---|---|
| 1 | 250 | 27.3 | 99.9 |
| 2 | 275 | 41.1 | 99.9 |
| 3 | 300 | 56.3 | 99.9 |
| 4 | 325 | 70.5 | 99.7 |

Example 9

Example 9 demonstrates the catalytic dehydrofluorination of HFC-245fa over the potassium doped $Al_2O_3$ catalyst in the presence of air.

5 cc Potassium doped $Al_2O_3$ catalyst, prepared as described in Preparation Example 2, was loaded into a ½ inch Hastelloy C 227 reactor tube. The catalyst was first treated with HF at 325° C. for about 13 hours. Then HFC-245fa was co-fed into the reactor tube with air at the 35 psig back pressure. HFC-245fa was fed at the rate of 4 ml/hr, and air was fed at the rate of 3 sccm. The temperature of the reactor tube was maintained at 250° C., 275° C., 300° C. and 325° C. respectively for a series of test runs and the effluent from the reactor tube was analyzed by GC and GC-MS. The results of the reaction at various temperatures are shown in Table 6.

TABLE 6

| Run | Temp. (° C.) | 245fa Conversion (%) | Selectivity to 1234ze (mole %) |
|---|---|---|---|
| 1 | 250 | 28.7 | 99.9 |
| 2 | 275 | 43.6 | 99.9 |
| 3 | 300 | 59.1 | 99.9 |
| 4 | 325 | 72.8 | 99.8 |

Example 10 (Comparative)

Example 10 demonstrates the catalytic dehydrofluorination of HFC-245fa over the $Cr_2O_3$ catalyst.

5 cc $Cr_2O_3$ (purchased from BASF with surface area of about 215 m²/g), after crushed and sieved to 12-20 mesh, was loaded into a ½ inch Hastelloy C 227 reactor tube and dried at 400° C. for 75 minutes under nitrogen. The catalyst was first actvated by HF at elevated temperatures. Then HFC-245fa was fed into the reactor tube at the rate of 2.5 ml/hr at the 35 psig back pressure. The temperature of the reactor tube was maintained at 225° C., 250° C., 275° C., 300° C. and 325° C. respectively for a series of test runs and the effluent from the reactor tube was analyzed by GC and GC-MS. The results of the reaction at various temperatures are shown in Table 7.

TABLE 7

| Run | Temp. (° C.) | 245fa Conversion (%) | Selectivity to 1234ze (mole %) |
|---|---|---|---|
| 1 | 225 | 9.8 | 98.7 |
| 2 | 250 | 15.3 | 99.2 |
| 3 | 275 | 23.1 | 99.4 |
| 4 | 300 | 33.3 | 99.5 |
| 5 | 325 | 46.9 | 99.3 |

Example 11 (Comparative)

Example 11 demonstrates the catalytic dehydrofluorination of HFC-245fa over the $Cr_2O_3$ catalyst in the presence of air.

5 cc $Cr_2O_3$ (purchased from BASF with surface area of about 215 m²/g), after crushed and sieved to 12-20 mesh, was loaded into a ½ inch Hastelloy C 227 reactor tube and dried at 400° C. for 75 min under nitrogen. The catalyst was first actvated by HF at elevated temperatures. Then HFC-245fa was co-fed into the reactor tube with air at the 35 psig back pressure. HFC-245fa was fed at the rate of 4 ml/hr, and air was fed at the rate of 3 sccm. The temperature of the reactor tube was maintained at 250° C., 275° C., 300° C. and 325° C. respectively for a series of test runs and the effluent from the reactor tube was analyzed by GC and GC-MS. The results of the reaction at various temperatures are shown in Table 8.

TABLE 8

| Run | Temp. (° C.) | 245fa Conversion (%) | Selectivity to 1234ze (mole %) |
|---|---|---|---|
| 1 | 250 | 16.8 | 99.6 |
| 2 | 275 | 25.0 | 99.6 |
| 3 | 300 | 35.9 | 99.5 |
| 4 | 325 | 48.4 | 99.4 |

Example 12

Example 12 demonstrates the catalytic dehydrofluorination of HFC-245fa over the magnesium doped $Al_2O_3$ catalyst.

5 cc Magnesium doped $Al_2O_3$ catalyst, prepared as described in Preparation Example 3, was loaded into a ½ inch Hastelloy C 227 reactor tube. The catalyst was first treated with HF at 325° C. for about 13 hours. Then HFC-245fa was fed into the reactor tube at the rate of 2.5 ml/hr at the 35 psig back pressure. The temperature of the reactor tube was maintained at 250° C., 275° C., 300° C. and 325° C. respectively for a series of test runs and the effluent from the reactor tube was analyzed by GC and GC-MS. The results of the reaction at various temperatures are shown in Table 9.

TABLE 9

| Run | Temp. (° C.) | 245fa Conversion (%) | Selectivity to 1234ze (mole %) |
|---|---|---|---|
| 1 | 250 | 16.3 | 99.9 |
| 2 | 275 | 24.3 | 99.9 |
| 3 | 300 | 34.6 | 99.9 |
| 4 | 325 | 46.7 | 99.9 |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification is to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination.

What is claimed is:

1. A process for making 1,3,3,3-tetrafluoropropene, comprising dehydrofluorinating 1,1,1,3,3-pentafluoropropane in vapor phase in the presence of a catalyst comprising a metal compound supported on alumina to produce a product mixture comprising 1,3,3,3-tetrafluoropropene, wherein said metal compound is selected from the group consisting of salts of sodium, potassium, zinc, magnesium, calcium, cobalt, copper, and chromium, and mixtures thereof, wherein the selectivity for the production of 1,3,3,3-tetrafluoropropene is at least 99%.

2. The process of claim 1 wherein said metal compound is selected from the group consisting of halides, bicarbonates, carbonates, nitrates, oxides, and oxyfluorides of sodium, potassium, zinc, magnesium, calcium, cobalt, copper, and chromium, and mixtures thereof.

3. The process of claim 1 wherein said catalyst is pretreated with a fluorinating agent.

4. The process of claim 3 wherein said fluorinating agent is HF.

5. The process of claim 1, 3 or 4, wherein said metal compound is selected from the group consisting of inorganic salts of potassium, zinc, and magnesium, and mixtures thereof.

6. The process of claim 5, wherein said metal compound is $ZnCl_2$.

7. The process of claim 6, wherein the process is conducted at a temperature of from about 250° C. to about 350° C.

8. The process of claim 5, wherein said metal compound is $KHCO_3$.

9. The process of claim 8, wherein the process is conducted at a temperature of from about 250° C. to about 350° C.

10. The process of claim 5, wherein said metal compound is $MgCl_2$.

11. The process of claim 1, wherein the process is conducted in the presence of a diluent.

12. The process of claim 1, wherein the process is conducted in the presence of oxygen or air.

13. The process of claim 1, wherein the selectivity to 1,3,3,3-tetrafluoropropene is at least about 99.5%.

14. The process of claim 1, further comprising recovering 1,3,3,3-tetrafluoropropene from the product mixture.

\* \* \* \* \*